United States Patent [19]

Sportelli et al.

[11] Patent Number: 4,472,637

[45] Date of Patent: Sep. 18, 1984

[54] COMPOSITE SHIELDING MEANS AND MOUNTING MEANS THEREFOR

[76] Inventors: Louis Sportelli, 175 Delaware Ave., Palmerton, Pa. 18071; James F. Winterstein, 1745 Highland Ave., S., Clearwater, Fla. 33516

[21] Appl. No.: 376,651

[22] Filed: May 10, 1982

[51] Int. Cl.³ ............................ G21F 1/00; G21F 3/00
[52] U.S. Cl. ..................................... 250/515.1; 378/65
[58] Field of Search ...................... 250/515.1; 378/148, 378/65, 156

[56] References Cited

U.S. PATENT DOCUMENTS

| | | | |
|---|---|---|---|
| 3,649,835 | 3/1972 | Brackenbrough et al. | 378/148 |
| 3,944,838 | 3/1976 | Gäde | 250/515.1 |
| 4,214,167 | 7/1980 | Gäde | 250/515.1 |
| 4,266,139 | 5/1981 | Sportelli et al. | 378/65 |

Primary Examiner—Bruce C. Anderson
Attorney, Agent, or Firm—John S. Roberts, Jr.

[57] ABSTRACT

A shielding means for an X-ray machine or the like comprised of a base plate which removably receives shielding members masking out selective portions of the base plate to control the passage of X-rays therethrough. The shielding members are of various types and are provided with adjustable and removable securing means to position the shields on the base plate. Removable mounting means position and maintain the shielding means on the X-ray machine.

9 Claims, 6 Drawing Figures

COMPOSITE SHIELDING MEANS AND MOUNTING MEANS THEREFOR

BACKGROUND OF THE INVENTION

The prior art is aware of various masking devices adapted to be associated with a source of energy, for example, an X-ray machine to shield various parts of a person's body or an object from the rays. These shields and their adaptability to either an energy source machine or the person or object can be seen in U.S. Pat. Nos. 2,426,884; 3,233,248; 3,631,249; 3,678,233; 3,944,838; 3,986,036; 4,082,957; and 4,266,139, which is a prior development of the present inventor. These patents typify the general state of the art in this area.

SUMMARY OF THE INVENTION

The present invention relates to shielding devices for X-ray machines, or the like, which can be readily assembled and mounted thereon in an economical, simple, and efficient manner. In essence, the shielding device is comprised of a base member provided with adjustable securing means adapted to receive and hold at least one masking plate thereon. These masks are of varying sizes and shapes and serve to prevent the passage of X-rays or the like onto a selected area of a person's body or an object thereby protecting the same. In one embodiment, the masking plate comprises a plurality of similar metallic sheets which can be selectively inserted into a housing so that the thickness thereof can be varied as desired. The housing and the sheets can be adjusted on the base plate. In another embodiment, a base member can be provided with a plate which can be trapezoidal in shape to vary the passage of X-rays from the edges toward the center of the same. In the simplest form, a shield, in the form of a human organ can be adjustably mounted on the base plate.

In all embodiments, the base member can be secured by means of a removable mounting member including rails mounting and positioning the base member on the X-ray machine or the like.

PREFERRED EMBODIMENT OF THE INVENTION

Figure 1:
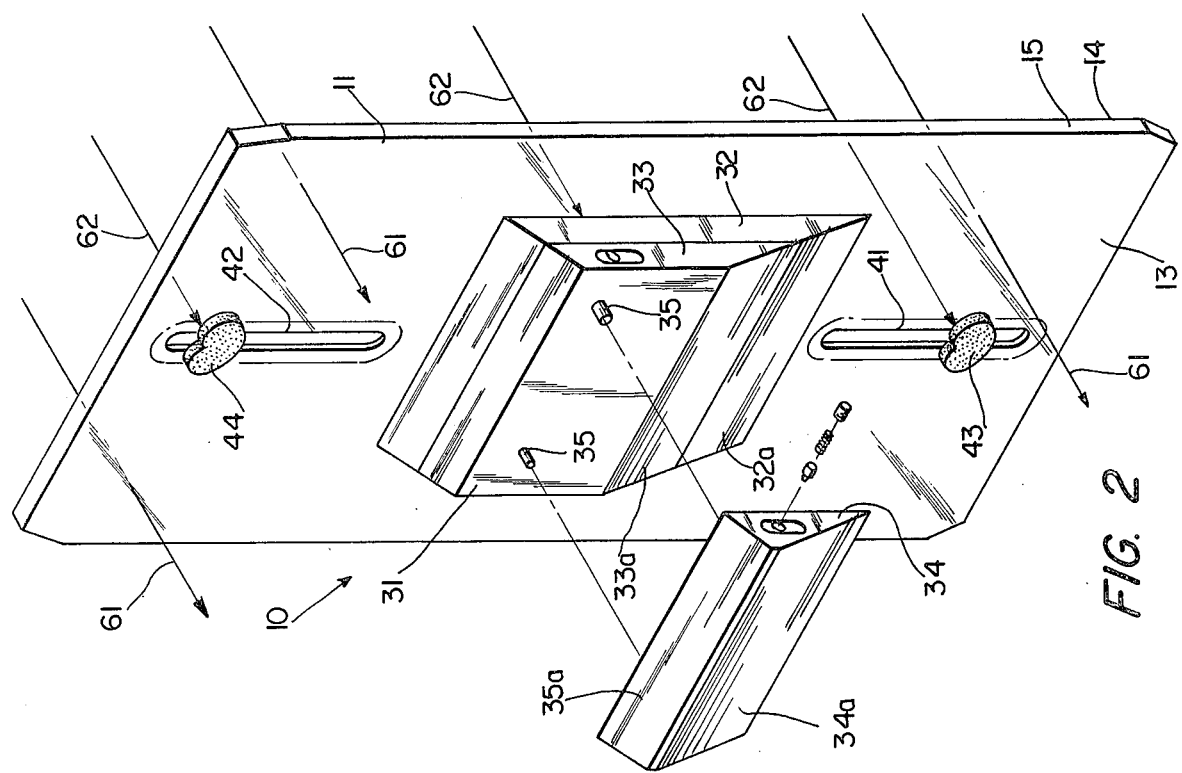
FIG. 1 is a perspective view showing the base plate and masking shields mounted on an X-ray machine.

The shield of the present invention is seen in FIG. 1 and is designated generally by the numeral 10 and is comprised of a base member 11 and a mounting member 12. The base 11 is made from plastic and is of generally rectangular configuration having front and rear surfaces 13, 14 separated by a thickness 15. The plate is disected by vertical and horizontal slots 16, 17 which provide a means of securing and adjusting a shield 21 and a masking plate assembly 22 thereon.

Figure 4:
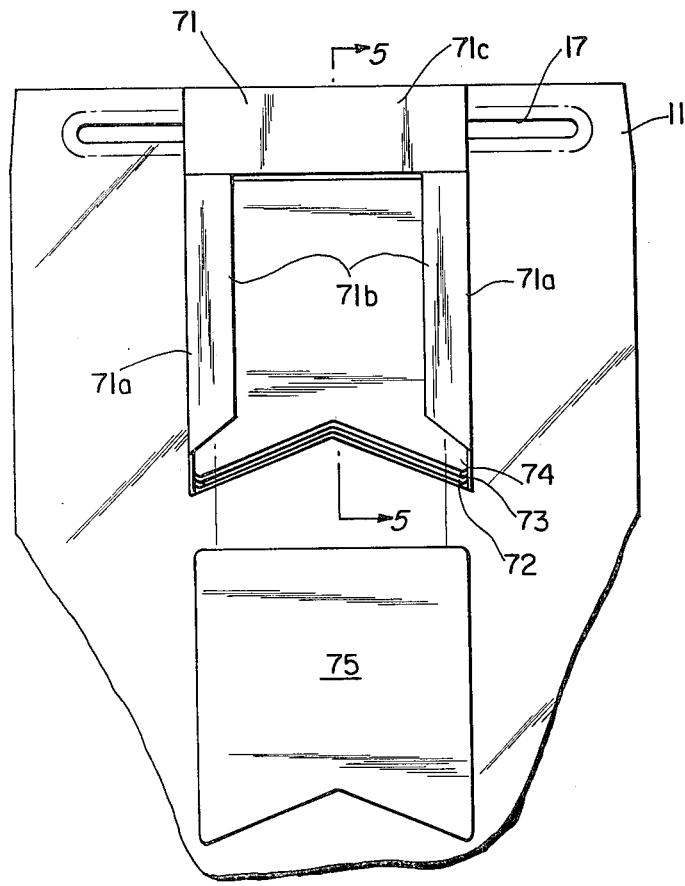
FIG. 4 is a perspective view of the housing adapted to receive and hold masking plates therein.
Figure 5:
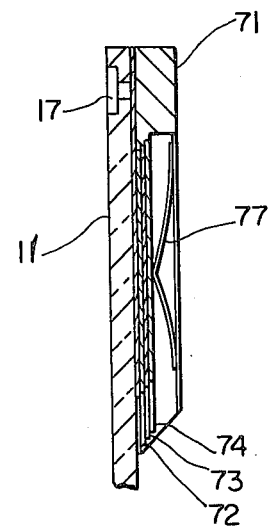
FIG. 5 is a sectional view of the housing taken along lines 5—5 of FIG. 4.

With reference to FIGS. 4 and 5, the details of the masking plate assembly are seen to be comprised of an open faced rectangular housing 71 having side wall 71a, 71a with inturned flanges 71b, 71b and closed at one end by a member 71c and open at the other end 71d which permit the insertion of one or a plurality of plates 72, 73, 74, 75. These plates 72-75 can be frictionally maintained within the housing or alternatively be held in place by a spring 77 (see FIG. 5) positioned within the confines of one of the side walls and flanges 71a, 71b. FIG. 4 shows shielding plate 75 prior to insertion in housing 71. With continuing reference to FIGS. 4 and 5, the housing 71, in turn, is removably secured and adjustably positioned on the base member 11 by disposing the same in the slot 17 by means of a fastener 17f such as a screw or bolt.

Figure 6:
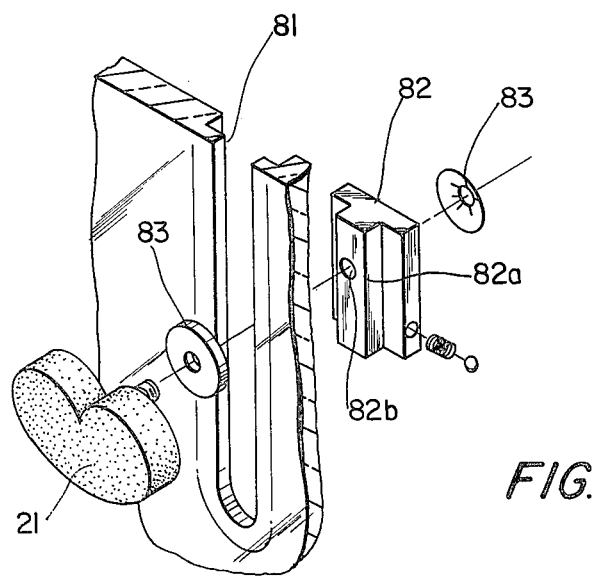
FIG. 6 is an exploded view of the details of the securing means for mounting a shield on the base plate.

As further seen in FIG. 1, the shield 21 is disposed in slot 16 and is adjustably maintained by the use of the fastening means shown in FIG. 6 which is seen to include a mounting plate 82 having a ridge 82a thereon extending into the slot 16. An opening 82b provided in the ridge 82a receives the pin 21a of the shield and is secured in place by washer 83.

Figure 2:
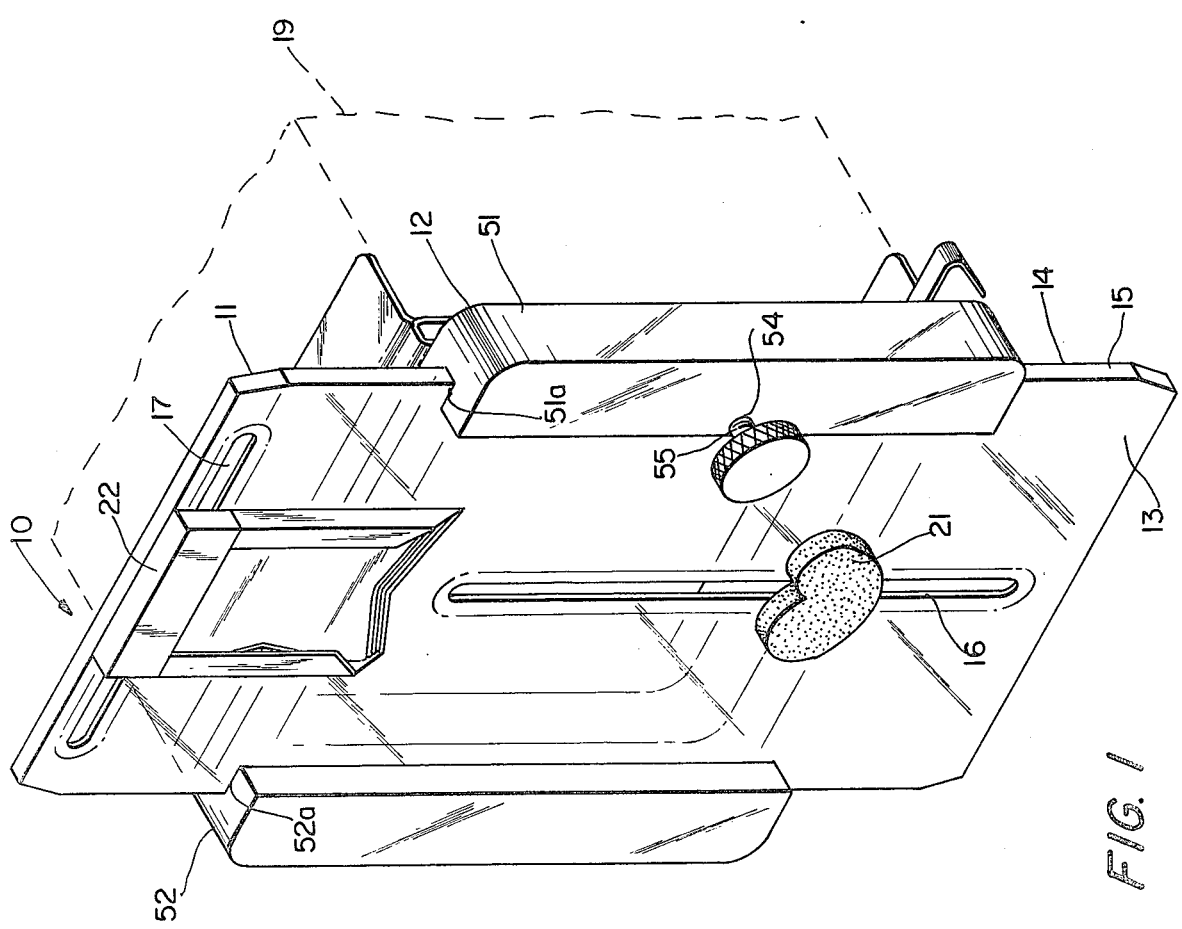
FIG. 2 is a perspective view showing another embodiment of a base plate with trapezoidal type shield.

A further embodiment of the invention is shown in FIG. 2 wherein the base plate 11 is provided with a trapezoidal shield 31 comprised of a plurality of sections and in this instance three sections 32, 33, 34 stacked one upon the other. Each of the elements 32, 33, 34 is fabricated from aluminum or stainless steel in a trapezoidal shape which can be used individually or be stacked one on the other by the use of pins and openings 35, 35a as shown in FIG. 2. Each of the elements has tapered edges 32a, 33a, 34a which permit a graduated resistance to the passage of the X-rays due to the increased thickness of the plate from these edges toward the main body thereof. Consequently, the selective stacking of the elements can vary the thickness of the overall shield. The base shield 32 as seen in FIG. 2 can be permanently affixed to the base plate 11 or mounted in an adjustable slot not shown.

The trapezoidal shield 31 is flanked by two slots 41, 42 having adjustable shields 43, 44 similar to that of shield 21 of FIG. 1 disposed therein.

Figure 3:
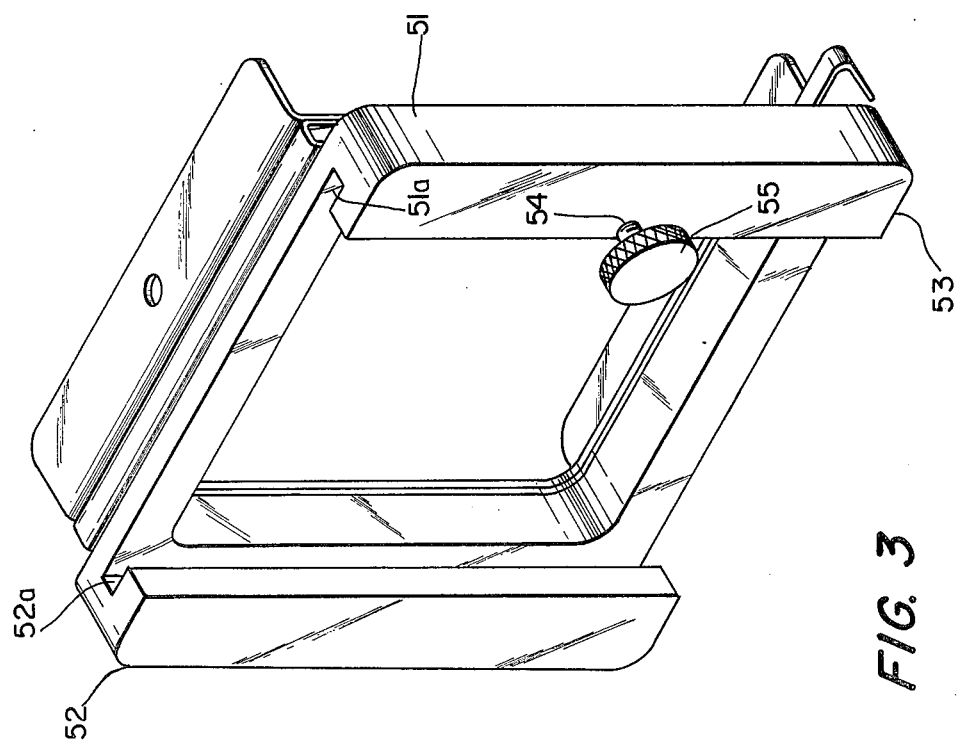
FIG. 3 is a perspective view of the mounting rails for the base plate.

The base member 11 in turn is provided with mounting means 12 adapted to be placed and maintained in front of an X-ray discharge opening or the like of a machine 19 shown in dotted outline in FIG. 1. As seen in FIG. 3 the mounting means 12 includes rails 51, 52 having recessed slots 51a, 52a within which the base plate 11 is slidably disposed. An opening 54 is provided in one rail 51 substantially medially thereof for receiving a threadable fastener 55 for releasably securing the base plate 11 in place. The base mounting member 12 is further secured to the machine by means of a metallic mounting member 56 which is rectangular in shape having openings 57, 58 which can be aligned with openings in the machine and maintained thereon by a threadable screw, bolt or other appropriate means.

In use and in all embodiments the base member 11 with any of the shields positioned thereon is positioned within the rails 51a, 52a affixed to the machine until it is disposed in front of the X-ray discharge opening. The threaded fastener 55 flushingly engages the front surface 13 of the base member 11 and frictionally locks the same in place.

As is apparent and as seen in FIG. 2, the rays 61 emanating from the X-ray source are seen to pass through the base member to the person or object disposed in front of the machine. However, certain of the rays 62 are seen to be stopped by the shields 31, 43, 44 and therefore that portion of the person or object will not be affected by the X-ray.

Therefore, it is seen that by providing the mounting rails and the composite shields of the present invention, a conventional X-ray machine can be simply modified to localize the passage of X-rays to any desired degree and to certain areas of a patent or object disposed in front of same.

I claim:

1. A support for a shielding member adapted to be positioned in the path of any energy source, comprising a support plate, a slot disposed in said plate, a first shielding member being disposed in said slot, and a means adjustably and removably securing said shielding means therein, and a second slot disposed substantially transversely to said first mentioned slot, and a second shielding member being disposed in said second slot and means adjustably and removeably securing said second shielding means therein, said second shielding member having a housing with retention means and at least one plate removably positioned and engaged therein by said retention means.

2. The support member of claim 1 wherein the housing member is constructed in a manner which provides a three-sided opening with inwardly disposed flanges to receive and position said shields.

3. The support member of claim 3 wherein each shielding plate is of rectangular configuration having a wedge shaped recess in one end thereof.

4. The support member of claim 1 wherein the said first shielding member is shaped in the form of a human organ so as to provide specific protection for said organ.

5. The removably securing means of claim 1 wherein said securing means include a base plate member disposed in said slot and having an opening receiving fastener means mounting the shielding member.

6. The support member of claim 1 wherein the second shielding member is of wedge like shape.

7. The support member of claim 1 wherein the shield is formed of a plurality of plates varying in thickness.

8. The support member of claim 1 wherein at least one slot means is provided adjacent the wedge to receive at least one additional shielding member.

9. The support member of claim 1 wherein the retention member is a spring.

* * * * *